United States Patent
Wehrli

(10) Patent No.: US 7,964,755 B2
(45) Date of Patent: Jun. 21, 2011

(54) CURCUMIN SYNTHESIS

(75) Inventor: Christof Wehrli, Witterswil (CH)

(73) Assignee: DSM IP Assets B.V., Heerlen (NL)

(*) Notice: Subject to any disclaimer, the term of this patent is extended or adjusted under 35 U.S.C. 154(b) by 85 days.

(21) Appl. No.: 12/295,010

(22) PCT Filed: Mar. 19, 2007

(86) PCT No.: PCT/EP2007/002403
§ 371 (c)(1),
(2), (4) Date: Jul. 29, 2009

(87) PCT Pub. No.: WO2007/110168
PCT Pub. Date: Oct. 4, 2007

(65) Prior Publication Data
US 2010/0312015 A1    Dec. 9, 2010

(30) Foreign Application Priority Data
Mar. 29, 2006 (EP) .................... 06006519

(51) Int. Cl.
*C07C 45/45* (2006.01)

(52) U.S. Cl. ............ 568/313; 568/325
(58) Field of Classification Search ......... 568/313, 568/325
See application file for complete search history.

(56) References Cited

U.S. PATENT DOCUMENTS
3,194,841 A     7/1965  Alphen et al.
5,679,864 A *  10/1997  Krackov et al. ............ 568/313

FOREIGN PATENT DOCUMENTS
WO        97/16403       5/1997

OTHER PUBLICATIONS
International Search Report for PCT/EP2007/002403, mailed Jun. 18, 2007.

* cited by examiner

*Primary Examiner* — Sikarl A Witherspoon
(74) *Attorney, Agent, or Firm* — Nixon & Vanderhye P.C.

(57) ABSTRACT

Process for the preparation of curcumin by condensation of vanillin with acetylacetone in the presence of boric acid and an aliphatic or araliphatic amine in a highly polar, aprotic solvent, under concomitant removal of water.

13 Claims, No Drawings

CURCUMIN SYNTHESIS

This application is the U.S. national phase of International Application No. PCT/EP2007/002403, filed 19 Mar. 2007, which designated the U.S. and claims priority to Europe Application No. 06006519.0, filed 29 Mar. 2006, the entire contents of each of which are hereby incorporated by reference.

The present invention relates to a synthesis of curcumin by condensation of vanillin with acetylacetone.

Curcumin, (E,E)-1,7-bis(4-hydroxy-3-methoxyphenyl)-1,6-heptadiene-3,5-dione, also known as turmeric yellow, is a natural dyestuff from the roots of *Curcuma* plants, e.g. *C. tinctoria, C. xanthorriza and C. domestica*, known since several hundred years. It is used as food colouring agent and has pharmacological, e.g. antimicrobial activity.

Curcumin is almost exclusively synthesised by condensation of acetylacetone with two molecules of vanillin in the presence of boric acid anhydride and/or borates.

British patent No. 914 047 (publ. 28.12.62) describes the condensation of vanillin with acetylacetone in the presence of 2 mole equivalents of trialkyl borates and 0.35 molequivalents boric oxide to give curcumin with yields from 16-80% of the theory. Best results (80% yield) at room temperature were obtained in ethyl acetate as solvent with 2 molequivalents tri-isopropyl borate in the presence of 0.35 molequivalent of boric anhydride and 0.1 molequivalent butylamine (Pabon, H. J. J., Recueil 83, 379-386 [1964]). However, the purity of the curcumin is not mentioned.

According to DE 1 280 849 curcumin is obtained by reaction of vanillin in molten form (heating to 120-130° C.) with acetylacetone in the presence of boric acid anhydride and a secondary amine and addition of glacial acetic acid, methanol and water. The yields are in the range of 19-28%. According to DE 1 282 642 vanillin is dissolved in dimethylsulfoxide, then boron oxide, acetylacetone and a secondary amine are added. After termination of the reaction at 80-85° C., aqueous acetic acid (5%) is added and after purification curcumin is obtained in a yield of 25% (purity 99.7%).

29 Jan. 2007 Mez

The addition of about molar amounts of alkyl borates and boric acid anhydride or boron oxide was necessary to remove the reaction water and to drive the reaction to completion. During the work-up and isolation the boron compounds formed uneconomic large amounts of boron containing wastewater making these procedures rather unattractive.

German Auslegeschrift DE 2 501 220 C describes the synthesis of boron esters of curcumin and of curcumin derivatives, from which curcumin can be obtained in an additional step. Boron esters of curcumin were obtained by reacting acetylacetone or a correspondingly substituted derivative thereof and an aromatic aldehyde and an α-hydroxi acid or a 1,2-glycol derivative with $B_2O_3$ in a solvent and/or an entrainer for azeotropic removal of water, in the presence of an cycloaliphatic or aliphatic amine as catalyst and a solvent and/or entrainers for azeotropic water removal. From the isolated boron complexes it was possible to obtain curcumin by hydrolysis with water or diluted acid. But the isolation of the boron complex and the additional hydrolysis step and the fact that no yields are given renders this process not attractive.

In U.S. Pat. No. 5,679,864 it is stated that the use of a water scavenger is needed to remove the water formed in the condensation, else the reaction does not proceed or the yields are substantially reduced. Scavengers mentioned are compounds that react with water like trialkylborates, trialkylphosphates, boron oxide, etc. U.S. Pat. No. 5,679,864 discloses further a process for the preparation of curcumin and certain derivatives thereof by five sequential steps, starting with reacting in an inert, highly polar aprotic solvent a boron or other metal complexing agent with a 2,4-diketone, adding an aromatic aldehyde, maintaining the solution at least 40° C. and adding 20-45 mole % of a primary or sec. amine and a water scavenger, admixing the resultant mass with dilute acid and separating the precipitated curcumin compound from the reaction mixture. The yields of pure curcumin according to this method hardly exceed 60%. Although many reaction parameters are varied this document does not give a guidance by which combination optimal results are obtained. The reported yield of raw curcumin (purity not given) without use of water scavenging hardly exceeded 50%. The addition of water scavenging compounds led to additional costs and waste. This renders the known processes not very attractive.

The increasing demand for curcumin prompted us to develop an economically and ecologically attractive synthesis of this compound in high purity and good yield. Therefore, the present invention relates to a new improved procedure which avoids the disadvantages of the methods of the state of the art, especially the use of alkyl borates. The water formed in the reaction mixture, determines together with the base the reaction rate. Surprisingly we found that the reaction procedes without addition of water scavenging agents, if one removes the reaction water by distillation. Therefore we developed the removal of the water by azeotropic distillation in the vacuum without addition of water removing agents, so that it is now possible to completely avoid the use of trialkoxyborates. As complexing agents only an approx. molar amount of boric acid is necessary in the reaction. Starting from vanillin curcumin can be obtained in approx. 75% yield.

In more detail the present invention relates to a process for the preparation of curcumin by condensation of acetylacetone with vanillin in a highly polar, aprotic solvent, in the presence of boric acid and of an aliphatic or araliphatic amine, and subsequent work up, characterised in that vanillin in the presence of an equimolar or nearly equimolar amount of boric acid and a catalytic amount of a primary amine of the formula R—$CH_2$—$NH_2$, to wherein R is $C_{1-19}$-alkyl or phenyl, optionally substituted with methyl, methoxy or halogen, in DMF, DMA or diglyme as solvent and, optionally, of an entrainer, is reacted with acetylacetone at a temperature of 50-85° C., preferably 50-60° C., at reduced pressure of 10-100 mbar, preferably 15-40 mbar, under concomitant removal of the reaction water by distillation, preferably as azeotrop. The invention also relates to curcumin whenever prepared by such a process.

In the present reaction equivalent molar amounts of vanillin and acetylacetone, viz. 2:1 moles, are normally used. However, variations of this value are possible without deviating from the gist of the present invention, e.g., within the range of 1.8-2.2:1. Unreacted vanillin can be recovered by extraction.

A "nearly equimolar" amount of boric acid to be used in the present process means an amount of about 0.85-1.25 mol equivalents of boric acid relative to vanillin. Best results are normally obtained within a range of 0.95-1.0 equivalents of boric acid per each equivalent of vanillin. Lower amounts decrease the yield of curcumin while larger amounts do not increase the yield further but slow down the reaction rate.

A "catalytic amount" of a primary amine means an amount of 10-40 mole %, preferably 20-30 mole %, per mole of acetylacetone. Examples of primary amines defined by the above formula are 2-methoxymethyl-amine, butylamine and benzylamine with the latter being preferred.

The preferred solvents to be used in the process of the present invention are dimethyl formamide (DMF), dimethyl acetamide (DMA) and diethyleneglycol-dimethylether (diglyme), of which DMF is the most preferred.

While in principle there is no need to use an entrainer in the present reaction its use is advantageous. The main function of the entrainer is to backwash the distilled acetylacetone. Well-suited entrainers are solvents with a boiling point slightly below the boiling point of acetylacetone used in the reaction and forming an azeotrop with water although not being miscible with water. Examples of such entrainers are n-pentanol, xylene, toluene and cyclohexane. Best results were obtained with xylene and n-pentanol which form azeotropes with water.

Since the selectivity and hence the yield increases with the decrease of the reaction temperature, the temperature should be as low as possible. The temperature may vary within the range of 40°-85° C., preferably 50-60° C., at a pressure of 100-10 mbar, preferably 40-20 mbar. Above 85° C. the side products increase substantially.

Upon completion of the reaction the boric acid, the solvents the catalyst have to be removed from the formed curcumin. The work up can be effected in accordance with methods well-known to the person skilled in the art, e.g., by extraction and/or crystallization. In accordance with one embodiment the reaction mixture is acidified and diluted with acetic acid to lower the viscosity and then the boric acid and the solvent and the catalyst is washed out with water. The resulting crystalline raw product can be purified further by slurrying in methanol under reflux to give pure curcumin (>98% [w %]) in about 66-69% yield. Alternatively, the reaction mixture can be diluted with an organic solvent such as ethyl acetate, acidified and washed with water. The ethyl acetate is evaporated and curcumin is slurried from methanol. Thus curcumin is obtained in about 60% yield with a purity more than 90%.

The invention is illustrated by the following examples.

EXAMPLE 1

In a 4 neck round bottom flask equipped with thermometer, mechanical stirrer, a short distillation column and a water separator (6 ml hold up) with a reflux cooler (cooling media −1° C.) were provided 12.0 g (194 mmole) of boric acid, 30.4 g (200 mmole) of vanillin, 6.6 g of m-xylene, 10.4 g (104 mmole) of acetylacetone, 15 ml of dimethylformamide and 20 ml of 1 m benzylamine in DMF (20 mmole).

The mixture was refluxed at 18 mmHg over the water separator for 2 hours at 50-53° C. The level of the phase boundaries in the water separator was held constant by approx. 5 ml water phase and 1 ml organic phase, by occasional removal of water. To the red solution were added 10 ml of 0.5 m benzylamine in DMF (5 mmole). The reaction mixture was refluxed for approx. 1-3 hours (see table below) until complete conversion of the intermediates.

If the reaction mixture got too viscous then the mixture was diluted with addition of dimethylformamide.

The reaction mixture was analysed by HPLC after different reaction times with the following results [w %]:

| Reaction time | Vanillin | Intermediates | Curcumin |
| --- | --- | --- | --- |
| 2 h | 21% | 15% | 54% |
| 3 h | 9% | 1% | 81% |
| 3.5 h | 9% | <0.2% | 83% |

EXAMPLE 2

Isolation of Curcumin from the Reaction Mixture

The reaction mixture of Example 1 was diluted with 55 ml of acetic acid 90%/water 10%. In a four neck reaction flask equipped with a mechanical stirrer, thermometer and a dropping funnel were provided 270 ml of water and 30 ml of conc. acetic acid. The dark red solution was added slowly at 80° C. The slurry was diluted with 270 ml of water at 80° C., cooled and stirred for 2 hours at ambient temperature, filtered through a Buchner funnel and washed with 270 ml of water. The residue was dried at 80° C. in the vacuum. 31.2 g of raw curcumin were obtained (content=87% [w %], yield=74 mole %)

EXAMPLE 3

Purification

The raw curcumin of Example 2 was suspended in 150 ml of methanol and refluxed for 30 minutes. The suspension was cooled and stirred for 2 hours at ambient temperature. The slurry was filtered with a Buchner funnel and washed with 50 ml of methanol. The yellow-orange filter cake was dried at 80° C. in the vacuum. 25.14 g of curcumin were obtained, m.p. 183°-184° C., (content 99% [w %], yield=68 mol %).

EXAMPLE 4

Isolation by Extraction and Crystallisation

The reaction mixture according to Example 1 was dissolved in a reaction flask with Teflon blade stirrer, thermometer and a reflux cooler in 300 ml of ethylacetate. The dark red solution was successively washed under reflux with 300 ml 3% of acetic acid in water, followed by two washings with each 100 ml of water. The organic phase was evaporated to dryness at the rotavapor (70° C., 20 mbar). The residue was suspended in 150 ml of methanol and refluxed for 30 minutes. The suspension was cooled and stirred for 2 hours at ambient temperature. The slurry was filtered with a Buchner funnel and washed with 50 ml of methanol. The yellow filtercake was dried at 80° C. in the vacuum. 23.41 g of curcumin were obtained (content=92% [w %], yield=59 mole %)

EXAMPLE 5

In a 4 neck round bottom flask equipped with thermometer, mechanical stirrer, a short distillation column and a water separator (6 ml hold up) with a reflux cooler (cooling media 10° C.) were provided 12.0 g (194 mmole) of boric acid, 30.4 g (200 mmole) of vanillin, 6.6 g of m-xylene, 10.4 g (104 mmole) of acetylacetone, 35 ml of dimethylformamide and 2.0 ml (20 mmole) of 1-butylamine.

The mixture was refluxed at 75 mmHg over the water separator for 1.5 hours at 79-82° C. The level of the phase boundaries in the water separator was held constant by approx. 5 ml water phase and 1 ml organic phase, by occasional removal of water. To the red solution were added 0.5 ml (5 mmole) of 1-butylamine and approx. 10 ml DMF. The reaction mixture was refluxed for approx. 1 hour until conversion of the intermediate. Curcumin was isolated from the reaction mixture according to Example 2. 32.8 g of curcumin were obtained (content=76% [w %], yield=68%)

EXAMPLE 6

In a 4 neck round bottom flask equipped with thermometer, mechanical stirrer, a short distillation column and a water separator (6 ml hold up) with a reflux cooler (cooling media 10° C.) were provided 12.0 g (194 mmole) of boric acid, 30.4 g (200 mmole) of vanillin, 6.6 g of m-xylene, 10.4 g (104 mmole) of acetylacetone, 15 ml of dimethylformamide and 20 ml (20 mmole) of 2-methoxyethylamine 1 n in DMF.

The mixture was refluxed at 32 mmHg over the water separator for 2 hours at 59°-62° C. The level of the phase boundaries in the water separator was held constant by approx. 5 ml water phase and 1 ml organic phase, by occasional removal of water. To the red solution were added 5 ml (5 mmole) of 2-methoxyethylamine 1 n in DMF. The reaction mixture was refluxed for approx. 1 hour until complete conversion of the intermediate. Curcumin was isolated from the reaction mixture according to Example 2. 29.4 g of curcumin were obtained (content=89% [w %], yield=71%).

The invention claimed is:

1. A process for the preparation of curcumin by condensation of acetylacetone with vanillin in a highly polar, aprotic solvent, in the presence of boric acid and of an aliphatic or araliphatic amine, and subsequent work up, comprising reacting vanillin in the presence of an equimolar or nearly equimolar amount of boric acid and a catalytic amount of a primary amine of the formula R—CH2-NH2, wherein R is C1-19-alkyl or phenyl, optionally substituted with methyl, methoxy or halogen, in DMF, DMA or diglyme as solvent and, optionally, of an entrainer, with acetylacetone at a temperature of 50-85° C. and at reduced pressure of 10-500 mbar, under concomitant removal of the reaction water by distillation.

2. The process of claim 1, wherein the amine is selected from the group consisting of butylamine, 2-methoxyethylamine and benzylamine.

3. The process of claim 1, further comprising using 10-35 mole % of amine relative to acetylacetone.

4. The process of claim 1, further comprising using benzylamine amount of 10-35 mole % relative to acetylacetone.

5. The process of claim 1, wherein the solvent is DMF.

6. The process of claim 1, further comprising using an entrainer and removing the reaction water as an azeotrope.

7. The process of claim 1, further comprising using an entrainer in an amount of 10-50% relative to vanillin.

8. The process of claim 1, further comprising using xylene as an entrainer.

9. The process of claim 1, further comprising using 90-100 mole % of B(OH)3 relative to vanillin.

10. The process of claim 1, wherein the work up is effected in situ without isolation of intermediates.

11. The process of claim 1, further comprising purifying curcumine by slurrying in methanol.

12. The process of claim 1, wherein the temperature is 50-60° C.

13. The process of claim 1, wherein the pressure is 15-40 mbar.

* * * * *